United States Patent [19]

Smith

[11] 4,344,433
[45] Aug. 17, 1982

[54] OSTOMATES APPLIANCE

[75] Inventor: Francis C. Smith, Fort Worth, Tex.

[73] Assignee: Smith's Ostomy Products, Inc., Fort Worth, Tex.

[21] Appl. No.: 186,144

[22] Filed: Sep. 10, 1980

[51] Int. Cl.³ .............................................. A61F 5/44
[52] U.S. Cl. ................................................ 128/283
[58] Field of Search ................... 128/283; 269/52, 322, 269/328

[56] References Cited

U.S. PATENT DOCUMENTS

| | | | |
|---|---|---|---|
| 3,083,704 | 7/1961 | Swearingen . | |
| 3,351,061 | 11/1967 | Nolan | 128/283 |
| 4,121,589 | 10/1978 | McDonnell | 12/283 |
| 4,187,850 | 2/1980 | Gust | 128/283 |

OTHER PUBLICATIONS

J.A.M.A., vol. 156, No. 15, Dec. 1954, p. 1399.

Primary Examiner—C. Fred Rosenbaum
Attorney, Agent, or Firm—Merchant, Gould, Smith, Edell, Welter & Schmidt

[57] ABSTRACT

An appliance (10) for facilitating replacement of a waste bag by an ostomy patient comprises a base (12), an upright post (14) removeably seated in said base, and a slideable collar (16) supported on an abuttment (18) on said post. One end of the post (14) includes an opening which covers the stoma and collects any seepage during the replacement procedure. The face plate and adhesive sealing ring are preassembled on the post (14) and collar (16), along with any reinforcing tape (32), after which the post is removed from the base (12) and positioned over the stoma so that the preassembly can be guided as a unit into engagement around the stoma.

15 Claims, 7 Drawing Figures

OSTOMATES APPLIANCE

TECHNICAL FIELD

The present invention relates generally to a medical apparatus, and more particularly to an apparatus and method for facilitating replacement of a waste bag by an ostomy patient.

BACKGROUND ART

Surgical procedures such as colostomies, cystostomies, urostomies and ileostomies involve rerouting of the colon or ureter so that waste materials can be discharged through an artificial opening formed in the patient's body. This artificial opening, called a stoma, is typically located in the abdomen and may be about 0.5 to 1.0 inch or more in diameter.

However, since ostomy patients have no sphincter control over their stomas, a receptacle or bag must be worn under the clothing to collect waste materials which discharge involuntarily. Disposable and semi-disposable bags for such purposes are available from several commercial sources. The disposable bags come as assembled units which are easily applied to the body.

In general, the semi-disposable bags are less expensive but somewhat more difficult to apply. Such bags are attached to the body over the stoma by means of a ring-like member known as a face plate and a sealing ring of double sided adhesive which must be assembled and positioned over the stoma with some precision to achieve a reliable attachment and seal. After removal of the filled bag, the common practice in the past has been to first clean and dry the stoma and surrounding skin area before application of the sealing ring to the skin, followed by connection of the face plate to the sealing ring and then attachment of a new bag to the face plate. It is most important that the skin area surrounding the stoma be kept clean and dry during replacement of the bag to avoid infection and to achieve a good connection between the skin, sealing ring and face plate. Adhesive tape is sometimes applied over the edges of the face plate and sealing ring for extra reinforcement. It will be appreciated that inadvertent disconnection of a bag can cause considerable inconvenience and embarrassment to an ostomy patient.

The prior techniques for replacing such waste bags have thus been characterized by a relatively tedious procedure requiring performance of various material positioning, peeling and pressing steps with respect to a stoma that may be difficult for the patient to observe directly. To see the stoma clearly in some cases may require a mirror the manipulation of which, along with the steps mentioned above, can be difficult.

Recently, U.S. Pat. No. 4,187,850 issued to Charles F. Gust for an apparatus to facilitate centering a sealing ring about a stoma while simultaneously keeping the surrounding skin area clean and dry by absorbing any waste material seeping from the stoma. The Gust apparatus, however, merely facilitates attachment of the sealing ring to the skin and is not adapted for remote preassembly of the sealing ring and face plate and then attachment of the resultant assembly to the body.

A need thus exists for an apparatus on which a sealing ring and face plate can be preassembled, and with a portion of which the resultant assembly can be quickly and easily guided into precise position while any waste material seeping from the stoma is simultaneously absorbed.

SUMMARY OF INVENTION

The present invention comprises a medical apparatus for use by ostomates which overcomes the foregoing and other difficulties associated with the prior art. In accordance with the invention, there is provided an appliance comprising a base, a post removeably seated in the base, and a moveable collar on the post. The post includes a circular flange thereon between the ends, and one end of the post is counterbored to fit over the stoma. The outside diameter of the post and inside diameter of the counterbore are dimensioned in accordance with the stoma size of a particular patient. In the preferred embodiment, a fitting can be employed to adapt posts of different sizes for mounting on a single base.

The appliance facilitates replacement of waste bags by ostomy patients by enabling remote preassembly of the adhesive sealing ring, face plate and any additional reinforcing tape on the collar and post while the post is mounted on the base. After preassembly, the post is detached from the base and used to guide the preassembly into engagement around the stoma while any waste material excreted from the stoma during the procedure is collected in the open end of the post. If desired, absorbent material can be placed in the open end of the post.

DESCRIPTION OF DRAWINGS

A more complete understanding of the invention can be had by reference to the following Detailed Description in conjunction with the accompanying Drawings, wherein.

DETAILED DESCRIPTION

Figure 1:
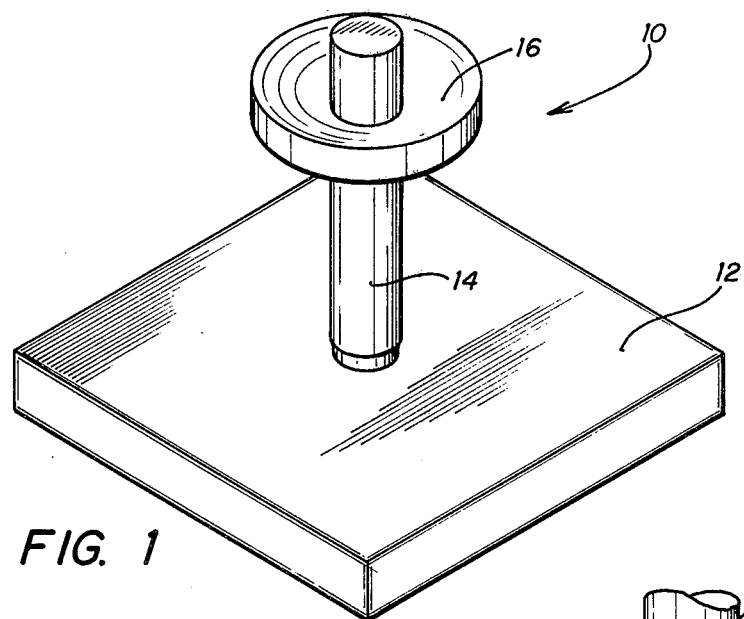
FIG. 1 is a perspective view of the ostomates appliance incorporating the invention.

Referring now to the Drawings, wherein like reference numerals designate corresponding elements throughout the views, and particularly referring to FIG. 1, there is shown an appliance 10 for use by ostomates which incorporates the invention. Appliance 10 comprises a base 12, an upright peg or post 14 removeably seated at one end in a corresponding opening formed in the base, and a collar 16 slideably positioned on the post. Appliance 10 can be constructed entirely from plastic, such as high density polyethylene, or other suitable material. As will be explained in greater detail hereinafter, appliance 10 is particularly adapted for use by an ostomy patient to facilitate replacement of a waste bag over his or her stoma.

Figure 2:
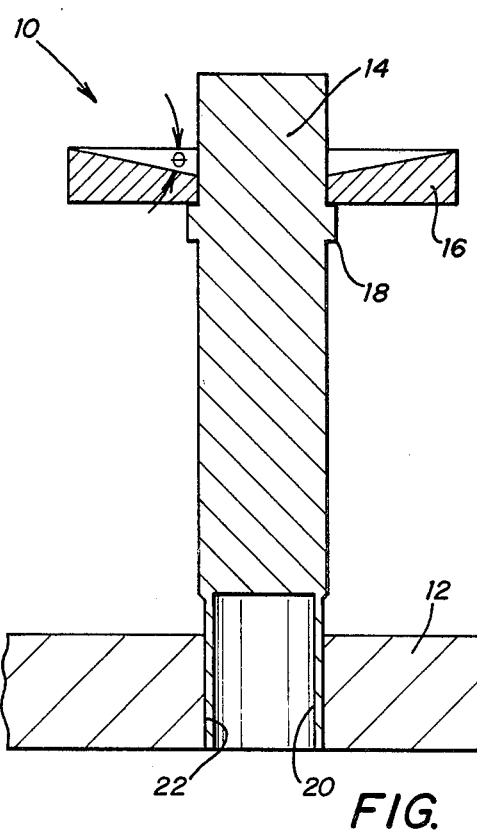
FIG. 2 is a cross sectional view of the appliance shown in FIG. 1.

The constructional details of appliance 10 can be seen in FIG. 2. Post 14, which may be approximately 4.5 inches in length, includes an integral collar or flange 18 and a counterbore 20 formed into one end thereof. Flange 18 is preferably located closer to the closed end of post 14. The circular sizes of post 14 and counterbore 20 are preferably dimensioned in accordance with the size of the stoma for a particular patient to provide 0.125 inch clearance around the stoma. For example, post 14 can be 0.500, 0.625, 0.750, 0.875 or 1.00 inch in outside diameter with counterbore 20 being 0.375, 0.500, 0.625, 0.750 or 0.875 inch, respectively, in inside diameter and about 1.0 inch deep. The purpose of counterbore 20 is to cover the stoma and collect any waste matter excreted therefrom during the bag replacement procedure. As shown in FIG. 2, the open end of post 14 is seated in a corresponding opening 22 extending through base 12. Post 14 can thus be seated at either end in opening 22 of base 12.

Collar 16, which is shown resting on flange 18 of post 14, includes flat and concave sides. The curvature of the concave side of collar 16 preferably corresponds to the curvature of the face plate (not shown in FIG. 2) required by a particular ostomy patient. For example, the angle of curvature $\theta$ of the concave side of collar 16 can be 9°, 10°, 20° or any other suitable angle. The purpose of collar 16 is to support the face plate as the adhesive sealing ring and any additional reinforcing tape preassembled on post 14 before being guided as a unit into attachment with the body around the stoma. Collar 16 can thus be slideable over either end of post 14, or slideable only on one end of the post.

While the preferred embodiment of appliance 10 incorporates a slideable collar 16 and fixed flange 18 on post 14, the collar could be secured to the post thereby combining the functions of the flange and collar.

Figure 3A:
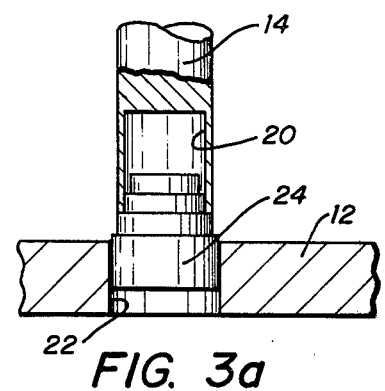
FIGS. 3a and 3b are views illustrating two alternate methods of adapting the post to the base.
Figure 3B:
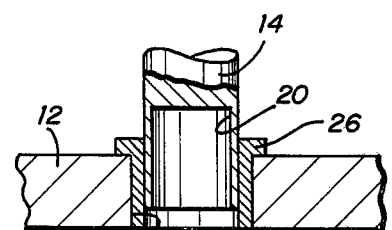

FIGS. 3a and 3b illustrate two adapters which can be utilized for adapting base 12 to support posts 14 of different sizes. FIG. 3a shows a plug 24 having a lower portion dimensioned for receipt by opening 22 in base 12, and a stepped upper male portion dimensioned for insertion into counterbores 20 of post 14 having predetermined sizes. FIG. 3b shows a hollow bushing 26 sized to receive the end of post 14.

Figure 4:
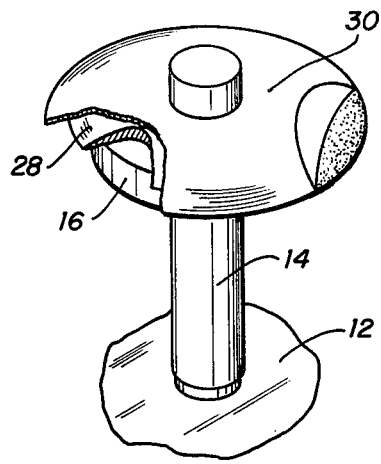
FIGS. 4–6 are illustrations of the method of replacing a waste bag in accordance with the invention.
Figure 5:
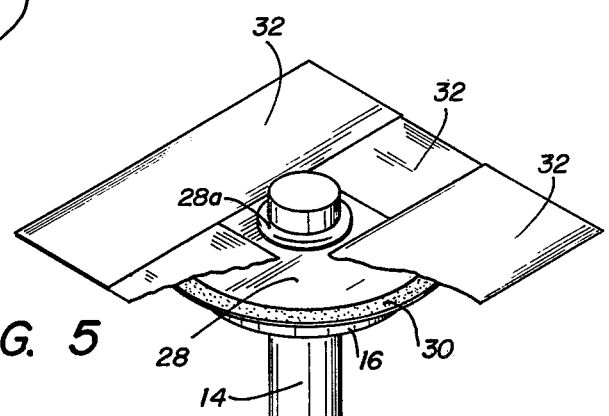
Figure 6:
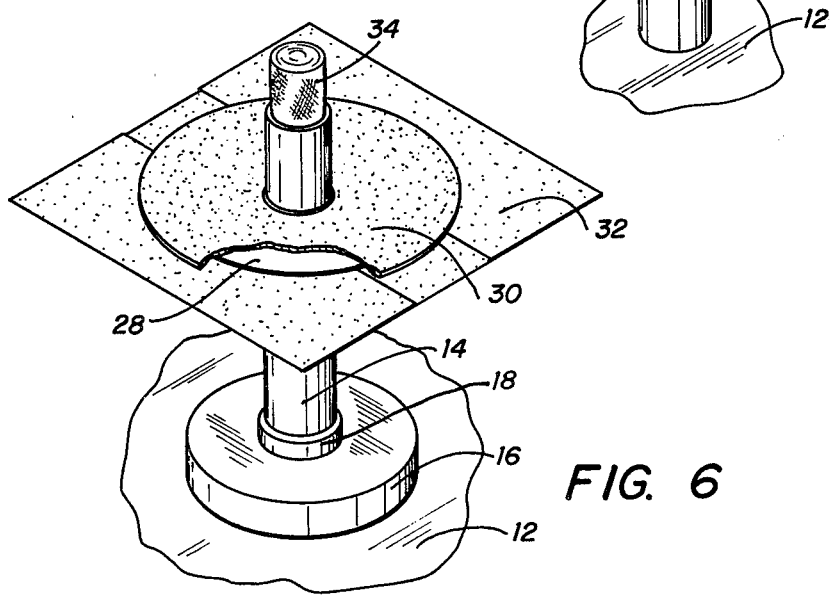

The method of replacing a waste bag in accordance with the invention is illustrated in FIGS. 4-6. Face plate 28 is first positioned over the one end of post 14 and on collar 16 with the body or inner side of the face plate facing upward. As shown, face plate 28 is first mounted on the closed end of post 14. The backing on one side of the double sided adhesive sealing ring 30 is then peeled back so that the sealing ring can be attached to the body side of face plate 28. Supporting face plate 28 on post 14 and collar 16 permits the patient to smooth out any bubbles or wrinkles which may develop between the face plate and ring so that there will be a good adhesive seal and connection. Thus, the first step involves remote attachment of sealing ring 30 directly to face plate 28 rather than to the skin.

After connection of adhesive ring 30 to the body side of face plate 28, the face plate is then removed from post 14, flipped over and repositioned on the post with the outer side thereof facing upwardly as shown in FIG. 5. If desired, a window of one-sided strips of adhesive tape 32 can then be formed around the face plate 28 and adhesive ring 30 for added reinforcement when the resultant preassembly is attached to the body. Tapes 32 should not overlap the flange 28a provided on the outer side of face plate 28 for connection with a plastic waste bag.

The resultant preassembly is then temporarily removed from post 14 so that the post can be turned over and reinserted into base 12 with the open end of the post facing upward as shown in FIG. 6 after which the preassembly is flipped over and repositioned thereon so that adhesive sealing ring 30 faces upward. The preassembly can rest directly on flange 18 of post 14 or on collar 16.

Absorbent material 34, such as gauze or the like, can then be inserted into counterbore 20 of post 14, if desired, before the remaining backing on the body side of adhesive sealing ring 30 is peeled away in preparation for attachment of the preassembly to the body. After the sealing ring 30 has been exposed, post 14 is lifted from base 12 and guided into engagement with the body such that counterbore 20 covers the stoma to catch any waste matter as face plate 28, ring 30 and tapes 32 are advanced down the post and into engagement with the skin surrounding the stoma. Once face plate 28 has been securely attached and post 14 has been removed, a new waste bag (not shown) can then be connected to flange 28a of the face plate.

Although the above procedure has been illustrated described in terms of beginning preassembly of the face plate 28, sealing ring 30 and tapes 32 on the closed end of post 14 before transferring the preassembled unit to the open end of the post, it will of course be understood that these components could be preassembled on the open end of the post to eliminate the transferring step.

From the foregoing, it will thus be appreciated that the present invention comprises an ostomates appliance having several advantages over the prior art. By means of the invention a face plate, adhesive sealing ring and adhesive reinforcing tape can be preassembled and then attached as a unit quickly and easily, thereby avoiding the prior difficulties of maintaining the skin area surrounding the stoma dry and clean during the replacement procedure. Other advantages will be apparent to those skilled in the art.

Although particular embodiments of the invention have been illustrated in the accompanying Drawings and described in the foregoing Detailed Description, it will be understood that the invention is not limited only to the embodiments disclosed, but is intended to embrace any equivalence, alternatives, modifications and/or rearrangements of elements falling within the scope of the invention as defined by the following Claims.

I claim:

1. Apparatus for facilitating preassembly and attachment of a face plate and adhesive sealing ring around a stoma, comprising:
   elongate post means having an open end and a closed end, the open end being adapted for receiving absorbent material;
   the open end of said post means being dimensioned for placement in predetermined surrounding relationship over the stoma;
   collar means mounted on said post means for supporting the face plate during attachment of the adhesive sealing ring thereto; and
   base means for releasably supporting said post at either end thereof remotely from the stoma.

2. The apparatus of claim 1, wherein said post is substantially cylindrical with the open end including a substantially cylindrical counterbore therein.

3. The apparatus of claim 1, wherein said collar is fixed to said post.

4. The apparatus of claim 1, wherein said collar is slideable along said post, and further including:
   an abuttment formed on said post between the ends thereof for supporting said collar.

5. The apparatus of claim 1, wherein said post supporting means comprises a plate of predetermined thickness having an opening therein for snugly receiving either end of said post.

6. Apparatus for facilitating preassembly and attachment of a face plate and adhesive sealing ring over a stoma, comprising:
- a substantially cylindrical post having open and closed ends, the open end of said post being adapted to receive absorbent material therein and dimensioned for placement in predetermined surrounding relationship over the stoma;
- collar means for placement over said post to support the face plate during attachment of the adhesive sealing ring thereto;
- abuttment means formed on said post between the open and closed ends thereof for supporting said collar means during preassembly of the face plate and sealing ring; and
- a base with an opening therein for receiving either end of said post and thereby releasably supporting said post remotely from the stoma.

7. The apparatus of claim 6, wherein said post, collar, abuttment means and base are all formed of plastic material.

8. The apparatus of claim 6, further including:
bushing means for placement in the opening of said base for connecting posts of different sizes thereto.

9. The apparatus of claim 6, wherein one side of said collar is curved in accordance with the curvature on one side of said face plate.

10. A method of attaching a waste bag to a stoma, comprising the steps of:
- (a) axially supporting a face plate on a central post, the post having an open end;
- (b) removing the backing from one side of a two-sided adhesive sealing ring;
- (c) engaging the exposed side of the sealing ring with the body side of the face plate;
- (d) removing the backing from the other side of said adhesive sealing ring;
- (e) guiding said post into engagement such that the open end of the post covers said stoma and collects any waste material therefrom;
- (f) moving said preassembled face plate and adhesive ring along said post and into adhesive engagement around the stoma;
- (g) removing said post; and
- (h) connecting the waste bag to the outer side of said face plate.

11. The method of claim 10, further including:
engaging at least one strip of adhesive tape over the margins of the outer sides of said face plate and sealing ring for reinforcement.

12. The method of claim 10, further including prior to step (e):
placing absorbent material in the open end of said post.

13. Apparatus for facilitating preassembly and attachment of a face plate and adhesive sealing ring over a stoma, comprising:
- substantially cylindrical post means having two ends, one end of said post means having an opening therein adapted to receive absorbent material and dimensioned for placement in predetermined surrounding relationship with the stoma;
- collar means adapted for movement along at least a portion of said post means to support the face plate, said collar means having a flat side and a concave side for receiving the face plate during attachment of the adhesive sealing ring thereto;
- flange means secured to said post means between the ends thereof for supporting said collar means thereon during preassembly of the face plate and sealing ring; and
- base means with an opening thereon for receiving either end of said post means and thereby releasably supporting said post means remotely from the stoma.

14. The apparatus of claim 13, wherein said post, collar, flange, and base are all formed of plastic material.

15. The apparatus of claim 13, further including:
bushing means for placement in the opening of said base for connecting posts of different sizes thereto.

* * * * *